(12) United States Patent
Bobek

(10) Patent No.: US 6,790,833 B2
(45) Date of Patent: Sep. 14, 2004

(54) ANTIFUNGAL AND ANTIBACTERIAL AGENTS

(75) Inventor: Libuse Bobek, Williamsville, NY (US)

(73) Assignee: The Research Foundation of the State University of New York, Amherst, NY (US)

( * ) Notice: Subject to any disclaimer, the term of this patent is extended or adjusted under 35 U.S.C. 154(b) by 64 days.

(21) Appl. No.: 10/215,168

(22) Filed: Aug. 8, 2002

(65) Prior Publication Data

US 2003/0069184 A1 Apr. 10, 2003

Related U.S. Application Data

(60) Provisional application No. 60/310,925, filed on Aug. 8, 2001.

(51) Int. Cl.[7] .............................................. A61K 38/00
(52) U.S. Cl. ............................. 514/12; 514/11; 514/14; 424/550; 435/7.1; 435/69.1; 435/183; 530/350
(58) Field of Search ................................. 435/7.1, 69.1, 435/29, 183; 424/550; 514/12, 11, 14; 530/350

(56) References Cited

PUBLICATIONS

Reddy et al. Structural features of the low–molecular–mass human salivary mucin. Biochem. J. (1992) 287: 639–643.*
RN 28554–07–6. Mucin MG 2 (human clone MG2–6–1 gene MUC 7 percursor). Search Report (Jan. 2, 2003): HCAPLUS, Registry.*

Satyanarayana et al. Divergent solid–phase synthesis and candidacidal activity of MUC7 D1, a 51–residue histidine–rich N–terminal domain of human salivary mucin (MUC 7). J. Peptide Res. (2000) 56: 275–282. [Also cited in IDS, Paper No. 4].*

Database PIR–73 on GenCore 5.1.3 Accession No: A48018, 1993. Reference 1 (Reddy et al., 1992): SEQ ID No. 4–9.*

Gururaja, et al., Candidacidal Activity Prompted by N–Terminus Histatin–like Domain of Human Salivary Mucin (MUC–7), BBA 1431 (1999) pp. 107–119.

Satyanarayana, et al., Divergent Solid–phase Synthesis and Candidacidal Activity of MUC7 D1, a 51–Residue Histidine–rich N–terminal Domain of Human Salivary Mucin (MUC7), J. Peptide Res., 2000, 56, pp. 275–282.

* cited by examiner

*Primary Examiner*—Brenda Brumback
*Assistant Examiner*—Maury A Audet
(74) *Attorney, Agent, or Firm*—Hodgson Russ LLP

(57) ABSTRACT

The present invention discloses peptides obtained from the MUCD1 domain of the saliva mucin glycoprotein MUC7. The peptides are between 8 and 20 amino acids in length and have a net positive charge. The peptides are obtained from the C-terminus of the MUC7D1 protein. These peptides are useful as antifungal and antibacterial agents. A method of using these peptides as antifungal and antibacterial agents is also disclosed.

8 Claims, 11 Drawing Sheets

| Peptides | Amino acid sequence | # of + charg. | (ratio) |
|---|---|---|---|
| Histatin-5: | D-S-H-A-K-R-H-H-G-Y-K-R-K-F-H-E-K-H-H-S-H-R-G-Y (1...10...20...24) | 13 | (0.25) |
| MUC7 D1: | E-G-R-E-R-D-H-E-L-R-H-R-R-H-H-H-H-Q-S-P-K-S-H-F-E-L-P-H-Y-P-G-L-L-A-H-Q-K-P-F-I-R-K-S-Y-K-C-L-H-K-R-C-R (1...10...20...30...40...51) | 5 | (.33) |
| 15-mer: | R-E-R-D-H-E-L-R-H-R-R-H-H-H-Q | 8 | (.23) |
| 34-mer: | S-P-K-S-H-F-E-L-P-H-Y-P-G-L-L-A-H-Q-K-P-F-I-R-K-S-Y-K-C-L-H-K-R-C-R | 7 | (.35) |
| 20-mer: | L-A-H-Q-K-P-F-I-R-K-S-Y-K-C-L-H-K-R-C-R | 7 | (.43) |
| 16-mer: | K-P-F-I-R-K-S-Y-K-C-L-H-K-R-C-R | 6 | (.50) |
| 12-mer: | R-K-S-Y-K-C-L-H-K-R-C-R | 6 | (.50) |
| 12-mer-2 (both C to A): | R-K-S-Y-K-A-L-H-K-R-A-R | 4 | (.33) |
| 12-mer-3 (RK to AA): | A-A-S-Y-A-C-L-H-K-A-C-A | 0 | |
| 12-mer-4 (no + charges): | A-A-S-Y-A-C-L-H-A-A-C-A | 0 | |
| 11-mer: | K-S-Y-K-C-L-H-K-R-C-R | 5 | (.45) |
| 10-mer: | S-Y-K-C-L-H-K-R-C-R | 4 | (0.4) |
| 8-mer: | K-C-L-H-K-R-C-R | 4 | (0.5) |
| 8-mer-N (N-term of 20-mer, 1 + charge): | L-A-H-Q-K-P-F-I | 1 | (0.125) |

```
                         SEQUENCE LISTING

<160> NUMBER OF SEQ ID NOS: 14

<210> SEQ ID NO 1
<211> LENGTH: 51
<212> TYPE: PRT
<213> ORGANISM: Homo sapiens
<220> FEATURE:
<223> OTHER INFORMATION: MUC7D1 domain of the saliva MUC7 protein

<400> SEQUENCE: 1

Glu Gly Arg Glu Arg Asp His Glu Leu Arg His Arg Arg His His
                 5                  10                  15

His Gln Ser Pro Lys Ser His Phe Glu Leu Pro His Tyr Pro Gly
                20                  25                  30

Leu Leu Ala His Gln Lys Pro Phe Ile Arg Lys Ser Tyr Lys Cys
                35                  40                  45

Leu His Lys Arg Cys Arg
                50

<210> SEQ ID NO 2
<211> LENGTH: 15
<212> TYPE: PRT
<213> ORGANISM: Homo sapiens
<220> FEATURE:
<223> OTHER INFORMATION: 15-mer; Amino acids 3-17 of the MUC7D1 peptide

<400> SEQUENCE: 2

Arg Glu Arg Asp His Glu Leu Arg His Arg Arg His His His Gln
                 5                  10                  15

<210> SEQ ID NO 3
<211> LENGTH: 34
<212> TYPE: PRT
<213> ORGANISM: Homo sapiens
<220> FEATURE:
<223> OTHER INFORMATION: 34-mer; Amino acids 18-51 of the MUC7D1 peptide

<400> SEQUENCE: 3

Ser Pro Lys Ser His Phe Glu Leu Pro His Tyr Pro Gly Leu Leu
                 5                  10                  15

Ala His Gln Lys Pro Phe Ile Arg Lys Ser Tyr Lys Cys Leu His
                20                  25                  30

Lys Arg Cys Arg

<210> SEQ ID NO 4
<211> LENGTH: 20
<212> TYPE: PRT
<213> ORGANISM: Homo sapiens
<220> FEATURE:
<223> OTHER INFORMATION: 20-mer; Amino acids 32-51 of the MUC7D1 peptide.

<400> SEQUENCE: 4

Leu Ala His Gln Lys Pro Phe Ile Arg Lys Ser Tyr Lys Cys Leu
```

```
                      5                  10                  15
His Lys Arg Cys Arg
                 20

<210> SEQ ID NO 5
<211> LENGTH: 16
<212> TYPE: PRT
<213> ORGANISM: Homo sapiens
<220> FEATURE:
<223> OTHER INFORMATION: 16-mer; Amino acids 36-51 of the MUC7D1 peptide.

<400> SEQUENCE: 5

Lys Pro Phe Ile Arg Lys Ser Tyr Lys Cys Leu His Lys Arg Cys
                 5                  10                  15
Arg

<210> SEQ ID NO 6
<211> LENGTH: 12
<212> TYPE: PRT
<213> ORGANISM: Homo sapiens
<220> FEATURE:
<223> OTHER INFORMATION: 12-mer; Amino acids 40-51 of the MUC7D1
      peptide.

<400> SEQUENCE: 6

Arg Lys Ser Tyr Lys Cys Leu His Lys Arg Cys Arg
                 5                  10

<210> SEQ ID NO 7
<211> LENGTH: 11
<212> TYPE: PRT
<213> ORGANISM: Homo sapiens
<220> FEATURE:
<223> OTHER INFORMATION: 11-mer; Amino acids 41-51 of the MUC7D1
      peptide.

<400> SEQUENCE: 7

Lys Ser Tyr Lys Cys Leu His Lys Arg Cys Arg
                 5                  10

<210> SEQ ID NO 8
<211> LENGTH: 10
<212> TYPE: PRT
<213> ORGANISM: Homo sapiens
<220> FEATURE:
<223> OTHER INFORMATION: 10-mer; Amino acids 42-51 of the MUC7D1 peptide.

<400> SEQUENCE: 8

Ser Tyr Lys Cys Leu His Lys Arg Cys Arg
                 5                  10

<210> SEQ ID NO 9
<211> LENGTH: 8
<212> TYPE: PRT
<213> ORGANISM: Homo sapiens
<220> FEATURE:
<223> OTHER INFORMATION: 8-mer; Amino acids 44-51 of the MUC7D1 peptide.

<400> SEQUENCE: 9

Lys Cys Leu His Lys Arg Cys Arg
                 5

<210> SEQ ID NO 10
<211> LENGTH: 8
<212> TYPE: PRT
<213> ORGANISM: Homo sapiens
```

-continued

```
<220> FEATURE:
<223> OTHER INFORMATION: 8-mer-N; Amino acids 32-39 of the MUC7D1 peptide.

<400> SEQUENCE: 10

Leu Ala His Gln Lys Pro Phe Ile
                5

<210> SEQ ID NO 11
<211> LENGTH: 12
<212> TYPE: PRT
<213> ORGANISM: Homo sapiens
<220> FEATURE:
<223> OTHER INFORMATION: 12-mer-2 variant of the 12-mer

<400> SEQUENCE: 11

Ala Ala Ser Tyr Lys Cys Leu His Lys Arg Cys Arg
                5                  10

<210> SEQ ID NO 12
<211> LENGTH: 12
<212> TYPE: PRT
<213> ORGANISM: Homo sapiens
<220> FEATURE:
<223> OTHER INFORMATION: 12-mer-3 variant of the 12-mer

<400> SEQUENCE: 12

Ala Ala Ser Tyr Ala Cys Leu His Ala Ala Cys Ala
                5                  10

<210> SEQ ID NO 13
<211> LENGTH: 12
<212> TYPE: PRT
<213> ORGANISM: Homo sapiens
<220> FEATURE:
<223> OTHER INFORMATION: 12-mer-4 variant of the 12-mer

<400> SEQUENCE: 13

Arg Lys Ser Tyr Lys Ala Leu His Lys Arg Ala Arg
                5                  10

<210> SEQ ID NO 14
<211> LENGTH: 24
<212> TYPE: PRT
<213> ORGANISM: Homo sapiens
<220> FEATURE:
<223> OTHER INFORMATION: Histatin-5

<400> SEQUENCE: 14

Asp Ser His Ala Lys Arg His His Gly Tyr Lys Arg Lys Phe His
                5                  10                  15
Glu Lys His His Ser His Arg Gly Tyr
            20
```

ANTIFUNGAL AND ANTIBACTERIAL AGENTS

This application claims priority to U.S. provisional application No. 60/310,925, filed on Aug. 8, 2001, the disclosure of which is incorporated herein by reference.

FIELD OF THE INVENTION

This invention relates generally to antifungal and antibacterial agents, and more particularly to peptides generated from a human salivary mucin glycoprotein, MUC7.

BACKGROUND OF THE INVENTION

Many currently available antimicrobial agents have undesirable toxic effects, and a wide spread use of these drugs has lead to rapid development of drug resistant strains which are the leading cause for treatment failure. The need for efficient antimicrobial agents increases with the emergence of pathogens resistant to current therapies. Among the different approaches to find novel, safe and effective antimicrobial agents, the discovery and use of naturally occuring antimicrobial peptides is attracting increasing attention. This is because unlike many currently used antimicrobial compounds, they show little or no toxicity toward mammalian cells and low tendency to elicit resistance. The functional and structural properties, and therapeutic potential of the naturally occurring antimicrobial peptides (ribosomally synthesized), have recently been reviewed (1,2). With respect to structure and function, magainins (3), dermaseptins (4), cecropins, (5) and mammalian defensins (22) have been best characterized (1, 6). The majority of these peptides exhibit a random structure in water and a well-defined structure (α-helical, β-sheet, extended structures and loops) in a simulated membrane-like environment (2). Their mode of antimicrobial action is not well understood. In most cases it is not mediated by receptors, but rather through peptide-microbial cell membrane lipid interaction, resulting in membrane permeation and cell lysis (7).

Human saliva has a fundamental importance in the host innate non-immune defense system against oral pathogens. Salivary mucins, together with other groups of salivary proteins (proline-rich proteins, cystatins, statherins and amylase) protect the oral cavity from microbial infections through more general protective mechanisms rather then the direct killing of microorganisms. The antimicrobial effect of mucins has largely been attributed to agglutination activity—trapping and clearing the microorganisms from the system. The selective binding of salivary mucins to microbial adhesins prevents the subsequent attachment of microorganisms to host surfaces (8,9). Conversely, mucins bound to tissues may serve as docking ports facilitating colonization of microorganisms like Streptococcus (10). Thus, salivary mucins play an intriguing, paradoxical role in the dynamics of the oral flora. The human saliva has been considered a potential source of naturally occurring antimicrobial agents. The human salivary non-immune defense system includes antimicrobial components such as the enzymes lactoferrin, lysozyme and peroxidase (11), as well as the histidine rich cationic peptides, histatins (12). Previous studies have shown that histatin-5 (24 amino acid peptide) (Hsn-5) possesses potent fungicidal activity in vitro against Candida albicans (C. albicans) (12). Further studies showed that Hsn-5 is targeted to mitochondria and that its cytotoxic activity depends on the metabolic activity of C. albicans. The killing of C. albicans by Hsn-5 is accomplished by an increase in membrane potential and permeability, and subsequent release of intracellular ATP (13,14). It was also shown that Hsn-5 and human neutophil defensin-1 kill C. albicans via a shared pathway (15).

Another component of human saliva is MUC7, a mucin glycoprotein consisting of 357 amino acid residues divided into 5 domains distinct in amino acid composition and function. Domain 1 constitutes the N-terminal 51 amino acid residues (MUC7 D1). While the parent MUC7 molecule does not exhibit fungicidal or bactericidal activity, it has been reported that synthetic 51-mer exhibits excellent in vitro cidal activity against 8 clinical important fungal strains (including azole-resistant and amphotericin B-resistant fungi). However, there are no reports of MUC7D1 having antibacterial activity. The size of the MUC7D1 is not amenable to its use as an effective antifungal or antibactericidal agent. Moreover, larger peptides are more difficult to synthesize and harder to purify. Accordingly, there is a continuing need to develop novel antifungal and antibactericidal agents.

BRIEF DESCRIPTION OF THE DRAWINGS

FIG. 7 is a schematic representation indicating the sequence and location of the peptides of the invention with respect to MUC7D1.

*albicans* (9A) and *C. neoformans* (9B). Results represent the mean of duplicate or triplicate experiments.

Figure 10:
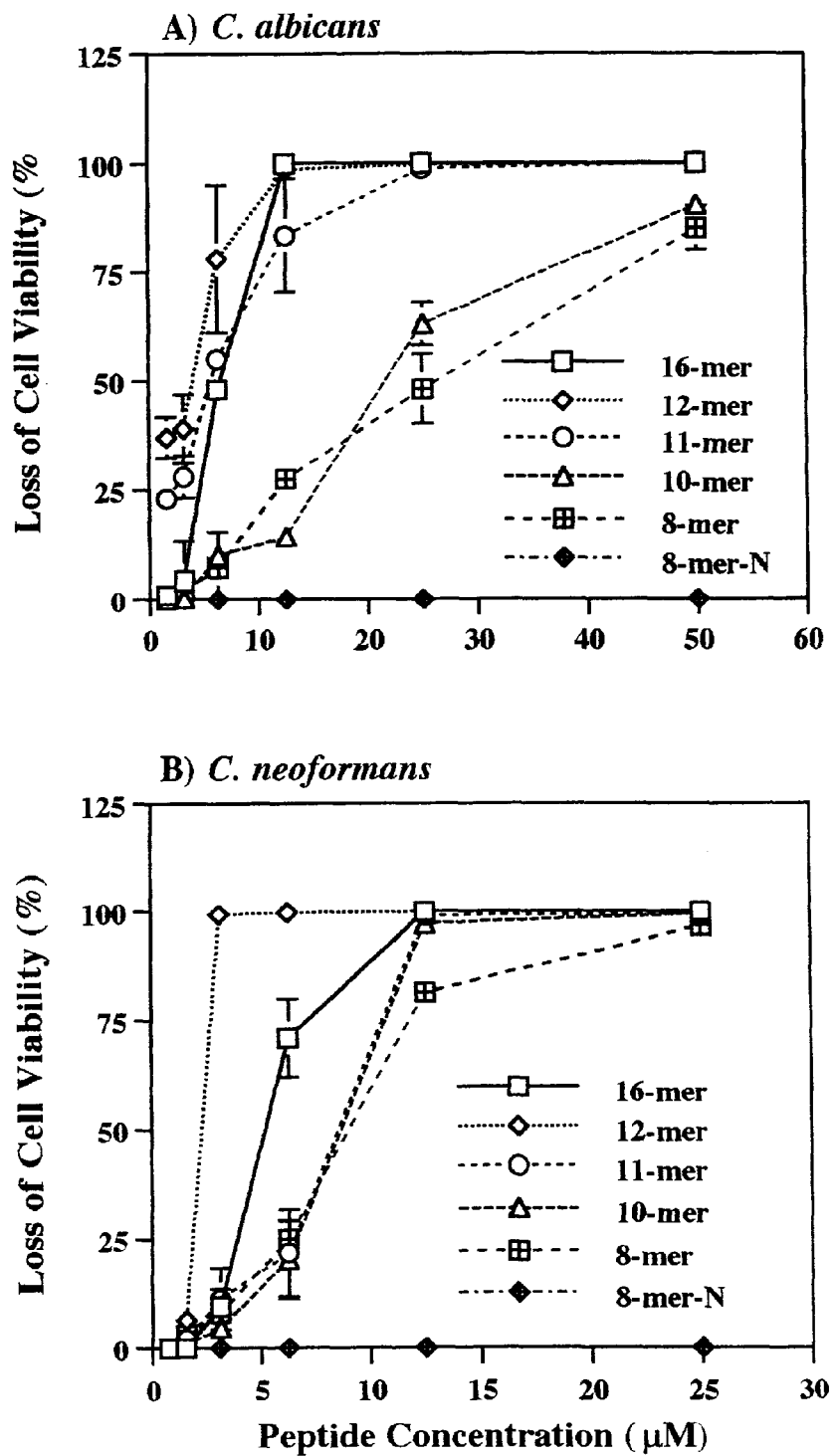

FIGS. 10A and 10B are representations of fungicidal activity of modified MUC7 12-mer peptides plotted as peptide concentration versus loss of cell viability. Results represent the mean of duplicate or triplicate experiments.

Figure 11:
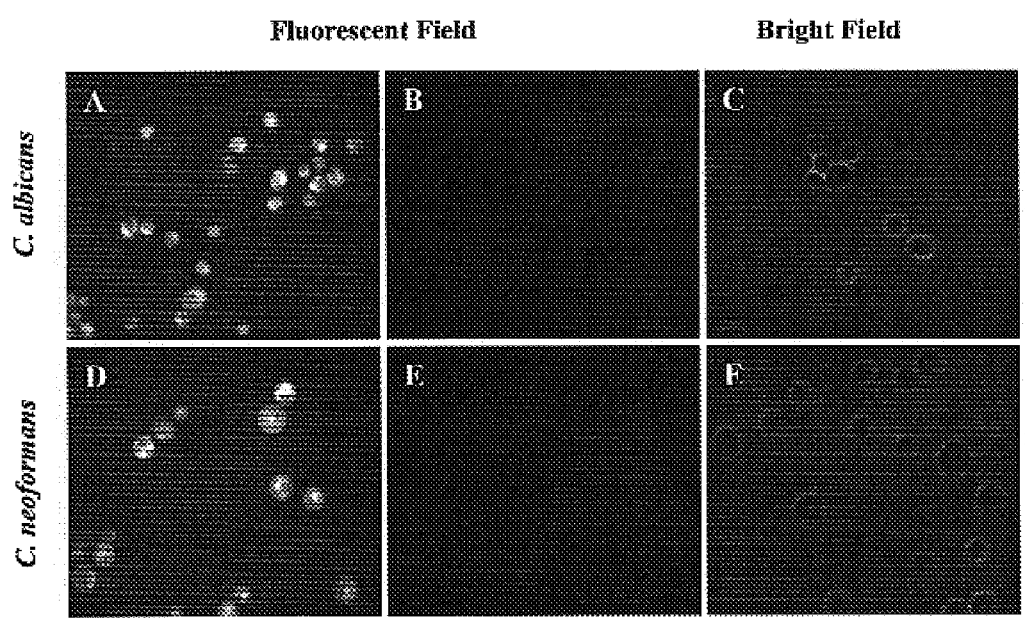

FIGS. 11(A–F) are photomicrographic representation of fluorescence light microscopy of internalization of MUC7 20-mer (A and D) and MUC7 12-mer-3 (B,C,E and F) by *Candida albicans* (A, B and C) and *Cryptococcus neoformans* (D, E and F). A, B, D and F represent fluorescent field. No internalization is observed with MUC 12-mer-3 (B and E) while internalization is observed with the positive control MUC7 20-mer (A and D). C and F are the bright field photomicrographs corresponding to B and E respectively.

SUMMARY OF THE INVENTION

The present invention provides antifungal and antibacterial peptides obtained from the human saliva mucin glycoprotein, MUC7. The peptides are obtained from the C-terminal region of the D1 domain fragment (MUC7D1) of MUC7. Useful peptides are between 8 to 20 amino acids in length and preferably contain a net positive charge. These peptides have been found to have broad-spectrum antifungal or antibacterial activity.

The present method also provides a method for using these peptides as antifungal and antibacterial agents.

DESCRIPTION OF THE INVENTION

The present invention provides antifungal and antibacterial peptides obtained from MUC7, a mucin glycoprotein. It was unexpectedly observed that peptides obtained from the C-terminus of the MUC7D1 domain exhibited antifungal and antibacterial activity. Peptides which did not contain the C-terminal portion of the MUC7D1 domain did not exhibit antifungal or antibacterial activity. Accordingly, the peptides are obtained from the C-terminal region of the MUC7D1. The peptides preferably contain a net positive charge and more preferably more than one net positive charge and still more preferably at least four net positive charges. Modifications of the peptides are also provided. Further, this invention also provides a method for the use of the antifungal and antibacterial peptides.

Figure 1:
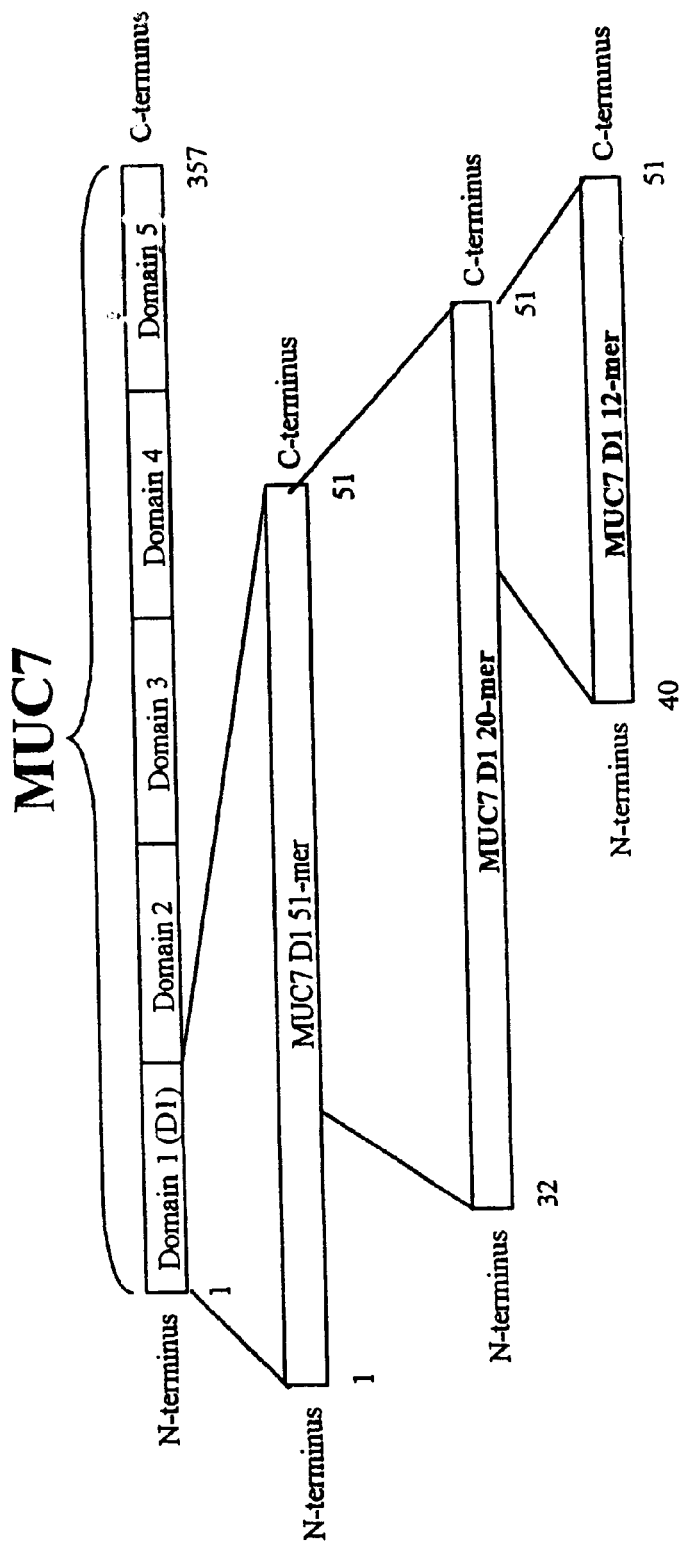
FIG. 1 is a schematic representation of the 5 domains of MUC7. The 51 amino acid domain 1 is termed MUC7D1.

MUC7 has 357 amino acids. Its sequence is divided into 5 domains D1–D5 (FIG. 1). D1 constitutes the N-terminal 51 amino acid residues (MUC7D1 51 mer) of the full protein. Its sequence is presented in SEQ ID NO.1. The numbering of amino acids used throughout this application refers to the sequence of MUCD1 as shown in SEQ ID NO.: 1, unless indicated otherwise. Exemplary peptides synthesized from the MUCD1 are shown in FIG. 7. These are:

- a 15-mer (amino acids 3–17)-SEQ ID NO.2;
- a 34-mer (amino acids 18–51)-SEQ ID NO.3;
- a 20-mer (amino acids 32–51)-SEQ ID NO.4;
- a 16-mer (amino acids 36–51)-SEQ ID NO.5;
- a 12-mer (amino acids 40–51)-SEQ ID NO.6;
- an 11-mer (amino acids 41–51)-SEQ ID NO.7;
- a 10-mer (amino acids 42–51)-SEQ ID NO.8;
- and an 8-mer (amino acids 44–51)-SEQ ID NO.9.

Some variants of the above were prepared as follows:

An 8-mer-N was prepared from the N-terminus of the 20-mer (amino acids 32–39; SEQ ID NO.10).

Three other 12-mers were synthesized as variations of the 12-mer. These are labeled as:

12-mer-2 (SEQ ID NO.11) where both arginine and lysine at position 40 and 41 of SEQ ID NO. 1 are replaced by alanine.;

12-mer-3 (SEQ ID NO.12) where arginine, lysine, lysine, lysine, arginine and arginine at positions 40,41, 44, 48, 49 and 51 respectively of SEQ ID NO.1 are replaced by alanine; and 12-mer-4 (SEQ ID NO.13) where both cysteines at positions 6 and 11 of SEQ ID NO.6 are replaced by alanine Peptides useful as antifungal or antibacterial agents are those which are at least 8 amino acids in length and which comprise at least the 8 C-terminal amino acids of MUC7D1, and substitutions thereof. An example of a permissible substitutions is alanine for cysteine. The peptides should have a net positive charge, preferably more than one net positive charge and more preferably 4 net positive charges. An example of a substitution is where cysteines in the 8 C-terminal amino acids are replaced by another neutral amino acid such as alanine.

The peptides of the present invention can be chemically synthesized. Thus polypeptides can be prepared by solid phase peptide synthesis, for example as described by Merrifield (16). The synthesis is typically carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are well known to those skilled in the art and include acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups are also removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In addition, the peptides can also be prepared by recombinant DNA technologies wherein host cells are transformed with proper recombinant plasmids containing the nucleotide sequence encoding the particular peptide. The peptides of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are well known in the art and can be found in standard references such as Sambrook et al. (17) and Ausubel et al. (18).

In general, a DNA sequence encoding a peptide of the present invention is operably linked to other genetic elements required for its expression, generally including a transcription promoter and terminator within an expression vector. The vector typically contains one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are available through commercial suppliers.

The peptides of the present invention can be formulated into compositions in pharmaceutically acceptable carriers for administration to individuals. For oral administration, the peptides can be formulated into a solid preparation such as tablets, pills, granules, powder, capsules and the like, or a liquid preparation such as solutions, suspensions, emulsions and the like. The pharmaceutical preparations for oral administration comprising one or more peptides of the present invention may also contain one or more of the following customary excipients: fillers and extenders including starches, lactose, sucrose, glucose, mannitol and silica; binders including carboxymethylcellulose, alginates, gelatine and polyvinylpyrrolidone; humectants including glycerine; disintegrating agents, including agar-agar, calcium carbonate and sodium carbonate; solution retarders, including paraffin; absorption accelerators including quaternary ammonium compound; wetting agents including cetyl alcohol or glycerine monostearate; adsorbents including kaolin and bentonite; lubricants including talc, calcium stearate and magnesium stearate and solid polyethylene glycols; colorants; flavourings; and sweeteners.

When the preparation is used for parental administration, the preparation is made in an injection formula. For the preparation of an injection formula, the solutions and emulsions can be in a sterile form which is isotonic with blood. The suspensions can contain in addition to the active peptide or peptides, preservatives, stabilizers, solubilizers, wetting agents, salts for changing the osmotic pressure or buffers.

The peptides of the present invention are useful as antifungal or antibacterial agents. The 12-mer peptides can be used against a broad spectrum of fungi and bacteria including, but not limited to, *Candida albicans, Candida glabrata* and their azole resistant counterparts, *Crytococus neoformans* and its amphotericin B-resistant counterpart, *Candida krusei, Saccharomyces cerevisiae*, and against *E. coli, Streptoccocus gordonii, Streptococcus mutans, Actinobacillus actinomycetemcimitans* and *P. gingivalis*. The optimal concentrations of the peptides can be obtained by determining the minimum inhibition concentrations (MICs) against bacteria and fungi. At the same time, toxicity studies can be carried out in vitro using cell culture techniques, in animals and by simple techniques such as the ability of the peptides to lyse blood. These and other advantages and the present invention will become clear from the following examples which are meant to be illustrative and are not intended to be restrictive in any way.

EXAMPLE 1

This embodiment, demonstrates the antifungal and antibacterial activity of the 20-mer peptide of SEQ ID NO:4. The antifungal and antibacterial activity was tested as follows.

Materials

Carbonyl cyanide m-chlorophenylhydrazone (CCCP) and sodium azide were purchased from Sigma Chemical Co. (St. Louis, Mo.). MitoTracker Red mitochondrial probe and 3,3'-dipropyl-2,2'-thiadicarbocyanine iodide (DiSC$_3$(5)) were purchased from Molecular Probes Inc. (Eugene, Oreg.). Sabouraud dextrose agar (SAB) and Tryptic soy agar (TSB) were from Difco Laboratories (Detroit, Mich.). Unlabeled, fluorescein isothiocyanate-labeled MUC7 20-mer and the functional domain of Hsn-5 used for transmembrane potential studies were purchased from Bio-Synthesis Inc. (Lewisville, Tex.). HPLC and mass spectrometry were performed by the company to analyze the purity of the peptides. The recombinant Hsn-5 was produced in *E. coli*, using pET–30b(+) vector. The cloning, expression, and purification of this peptide were as previously described (19) and its sequence is is disclosed as SEQ ID NO:14.

Yeast and Fungal Culture

Azole-sensitive (# 2-76) and azole-resistant (# 12-99) clinical isolates of *C. albicans* were a gift from Dr. Theodore C. White (University of Washington and Seattle Biomedical Research Institute, Seattle, Wash.). An azole-sensitive *Candida glabrata* (*C. glabrata*) was purchased from ATCC (ATCC 90030) and its azole-resistant counterpart, clinical isolate 65C, was obtained from Dr. John E. Bennett (National Institute of Allergy and Infectious Diseases, Bethesda, Md.). A clinical isolate of *Candida krusei* (*C. krusei*) was obtained from the Erie County Medical Center, Buffalo, N.Y. Amphotericin B-sensitive (CN2) and -resistant (CN2843) *C. neoformans* strains were obtained from AIDS patients with cryptococcal meningitis and were generously provided by Dr. John H. Rex (University of Texas Medical School, Houston, Tex.). Additionally, *Saccharomyces cerevisiae* (*S. serevisiae*) strain S288C was provided by Dr. D. Kosman, Department of Biochemistry, University at Buffalo, the State University of New York. All fungi were streaked and grown on SAB plates at 37° C., except *S. cerevisiae*, which was grown at 30° C. until large colonies were formed. One colony was then picked and resuspended in Na phosphate buffer (pH 7.4) and the concentration was adjusted to 1×10$^5$ cell/ml for the antifungal assay described below.

Bacterial Strains and Culture Conditions

The following bacterial strains were tested: *Streptococcus mutans* (*S. mutans*) GS-5, *Streptococcus gordonii* (*S. gordonii*) Challis, *Escherichia coli* (*E. coli*) HB101, *Pseudomonas aeruginosa* (*P. aeruginosa*) ATCC 17648, *Actinobacillus actinomycetemcomitans* (*A. actinomycetemcomitans*) NCTC9710, *Porphyromonas gingivalis* (*P. gingivalis*) 381 and W50. *S. mutans, S. gordonii, A. actinomycetemcomitans* and *P. aeruginosa* were grown anaerobically by candle jar extinction at 37° C. on TSB plates. *P. gingivalis* was grown in anaerobic chamber at 37° C. on sheep blood agar plates. *E. coli* was grown aerobically at 37° C. on LB agar plates.

Antifungal and Antibacterial Activity Assays

Two fold serial dilutions of each peptide (ranging from 100 μM down to 1.5625 μM) in 20 μl of 10 mM Na phosphate buffer, pH 7.4, were incubated with an equal volume of bacterial or fungal strain (10$^5$ cells/ml) for 1.5 hours at 30° C. for *S. cerevisiae* and 37° C. for the rest of strains tested. At the end of incubation, the samples were diluted 20 fold and aliquots (~120 cells) of each sample were plated on appropriate plates depending on the strain tested, as indicated above. Plates were incubated for 1 to 7 days aerobically or anaerobically, depending on the strain tested. Colonies were then counted, and the loss of cell viability was plotted as a function of protein concentration. Fungicidal activities against C. albicans and C. neoformans were also tested at 4° C.

To test the effect of inhibitors of oxidative phosphorylation in the mitochondrial system on peptide-induced killing, C. albicans and C. neoformans (CN2) were preincubated with either 20 mM sodium azide or 300 μM CCCP for 2 hours at 37° C. The cidal assays were then carried out as described above. In separate control experiments, both inhibitors were evaluated for their toxicity toward C. albicans and C. neoformans (CN2) in the absence of peptides. At these concentrations, neither compound had any cidal effect. In addition, the fungicidal activities of MUC7 20-mer and Hsn-5 (25 μM) in 10 mM Na phosphate buffer (pH 7.4) in the presence of varying concentrations (1–50 mM) of $Ca^{++}$ (as $CaCl_2$) or $Mg^{++}$ (as $MgCl_2$) were examined.

Statistical Analysis $ED_{50}$ values (molar concentrations of peptides required to kill half of the maximal number of cells) and 95% confidence limits of $ED_{50}$ values were determined by the procedure PROBIT (SPSS software package 6.1.2 for Macintosh). A time course study of peptide-induced killing was statistically analyzed by student t-test.

Analysis of Fungal Transmembrane Potential

Peptide-induced permeabilization of C. albicans and C. neoformas cell membranes was monitored by measuring changes in transmembrane potential. Measurements were carried out using the transmembrane potential sensitive dye 3,3'-dipropyl-2,2'-thiadicarbocyanine iodide ($DiSC_3(5)$). Fungi were grown overnight on SAB plates and resuspended in 10 mM Na phosphate buffer pH 7.4 at a concentration of $1 \times 10^5$ cells/ml. Dye was diluted in ethanol to achieve a final concentration of 714 nM. Ethanol in such a low dilution does not have any significant effect on the killing of the cells, and thus on the mechanism by which 20-mer works. The use of this dye in fungal cells to monitor changes in permeabilization is reliable and well documented. This cationic dye accumulates on membranes, is translocated into the lipid bilayer and aggregates within the confined membrane interior. Once aggregated inside the cell, the molecules interact with each other, losing energy, and decreasing fluorescence through a process called quenching. If permeabilization occurs, dye is released into the medium and it regains its fluorescent properties, allowing it to be detected. Experiments were carried out using a spectrofluorimeter (Perkin Elmer LS 50 B). A water bath and circulator was connected to the machine. Cells were incubated with dye at 37° C. for 2 hours in a Dry Bath Incubator (Fisher Scientific), and afterwards in a 700 μl fluorescence cuvette to maintain the samples at 37° C. Temperature was monitored with a thermometer (YSI Precision 4000A). Equilibration time was determined by monitoring the cell/dye suspensions with the spectrophotometer before experiments were conducted. A time drive application was used and samples were monitored at excitation and emission wavelengths of 633 nm and 666 nm respectively. At time 0 peptide samples were added at concentrations of 18 μM to cells preloaded with dye. Experiments were monitored over a 1500 second time interval. Data was graphically displayed as a function of fluorescence intensity over time, as determined by the following equation: Fluorescence Intensity=$\phi I_0(1-e^{\epsilon bc})$ where $\phi$ is quantum efficiency, $I_0$ is the incident radiant power, $\epsilon$ is the molar absorptivity, b is the path length of the cell and c is the molar concentration of the fluorescent dye.

Fluorescence Light Microscopy

The internalization of MUC7 20-mer into fungi was visualized in C. albicans and C. neoformans. Untreated cells ($10^7$) or cells preincubated with 20 mM sodium azide, 300 μM CCCP, 50 mM $Ca^{++}$ or 50 mM $Mg^{++}$ were then treated with 50 μM FITC-MUC7 20-mer for 45–90 minutes in 100 μl of Na phosphate buffer (10 mM, pH 7.4) at 37° C. Untreated cells were also incubated with 50 μM FITC-MUC7 20-mer at 4° C. The cells were then extensively washed with phosphate buffer, concentrated and resuspended in the same buffer. The cell suspension was then quickly mounted on slides with sealed cover-slips. Fluorescence light micrographs were made on a Nikon Optiphot microscope, with a fluorescent light source.

Confocal Co-Localization Studies

The intracellular localization of FITC-MUC7-20mer was investigated in a double-labeling experiment using MitoTracker Red mitochondrial probe. C. albicans and C. neoformans were incubated with 500 nM MitoTracker Red in 10 mM Na phosphate buffer, pH 7.4 for 15 minutes at room temperature, washed three times with the same buffer, and subsequently incubated with 50 μM FITC-MUC7 20-mer. After 20 min. incubation at 37° C., the suspension was washed with phosphate buffer extensively. The cell suspension was then quickly mounted on slides with sealed cover-slips. Confocal fluorescence microscopy was performed with a BioRad MRC-1024 confocal microscope system with Krypton-argon laser which outputs 488, 568 and 647 nm excitation line and Nikon upright epifluorescence microscope (Zeiss 60x oil immersion planApp objective with 1.4 numerical aperture).

Results

Broad-Spectrum Antifungal and Antibacterial Activities of MUC7 20-mer

As shown in Table 1, MUC7 20-mer shows potent antifungal activity against a variety of fungi including C. albicans, C. glabrata, C. krusei, C. neoformans and S. cerevisiae. In addition, it is also active against several drug resistant strains, including azole resistant C. albicans, fluconazole resistant C. glabrata and amphotericin B resistant C. neoformans. Its potency against all fungi tested compares to or exceeds that of full-length MUC7 domain 1 (51-mer) (20). In order to rule out the non-specific nature of this activity, insulin chain A, another unrelated peptide of the same chain length, was assayed. This peptide had no cidal activity (data not shown). A time-course killing experiment determined that MUC7 20-mer is able to kill both C. neoformans and C. albicans much more rapidly than Hsn-5 does ($p<0.05$) (Table 2). In addition, 20-mer kills C. neoformans faster than C. albicans ($p<0.05$). After a 5-minute incubation at 6.25 μM concentration, 97% of the C. neoformans populations was killed versus 32% of C. albicans cells.

MUC7 20-mer displays potent antibacterial activity against S. mutans, S. gordonii, E. coli and P. gingivalis, with $ED_{50}$ less than 3 μM, and A. actinomycetemcomitans and P. aeruginosa, with $ED_{50}$ value less than 5 μM (Table 1). In contrast, Hsn-5 had an $ED_{50}$ of 92 μM against S. mutans, and only induced 24% loss of cell viability at the highest concentration tested (100 μM) against A. actinomycetemcomitans (Table 1). Streptomycin and insulin chain A were used as positive and negative controls, respectively in the experiments against S. mutans and A. actinomycetemcomitans. No killing was detected with insulin chain A. The $ED_{50}$ of streptomycin against A. actinomycetemcomitans is 2.7 μM, and against S. mutans is 64 μM (Table 1).

TABLE 1

ED$_{50}$ of MUC7 20-mer and Hsn-5

| | ED$_{50}$ [μM] (95% confident limit) | |
|---|---|---|
| Strains | 20-mer | Hsn-5 |
| Fungi: | | |
| C. albicans | 5.85 (4.17–8.67) | 6.68 (6.05–7.37)¶ |
| C. glabrata | 5.02 (3.75–8.22) | 38.7 (30.8–50.7)¶ |
| C. krusei | 5.16 (4.17–6.40) | 6.47 (5.79–7.55)¶ |
| C. neoformans | 4.05 (3.16–5.81) | 3.71 (1.92–5.60)¶ |
| S. cerevisiae | 5.23 (4.01–6.76) | 74.0 (58.0–101.)¶ |
| C. albicans (azole-res) | 2.40 (1.73–3.08) | 6.40 (5.59–7.32)¶ |
| C. glabrata (fluconazole-res) | 12.3 (9.06–17.1) | 85.3 (78.4–94.0)¶ |
| C. neoformans (Amphetericin B-res) | 4.29 (3.59–4.26) | 3.72 (2.90–4.87)¶ |
| Bacteria: | | |
| A. actinomycetemcomitans* | 4.37 (3.74–5.04) | >100 |
| E. coli | 1.61 (1.09–2.14) | not tested |
| P. aeruginosa | 4.41 (3.65–5.19) | not tested |
| S. mutans* | 1.39 (1.00–1.90) | 92.0 (85.1–99.3) |
| S. gordonii | 2.43 (0.60–6.58) | not tested |
| P. gingivalis | <1.00 | not tested |

¶The data on Hsn-5 is from a previously published study (Ref 20).
*The ED$_{50}$ of streptomycin against S. mutans is 64 μM, and against A. actinomycetemccomitans is 2.7 μM.

TABLE 2

| | Loss of Cell viability (%) | | | |
|---|---|---|---|---|
| | C. albicans | | Hsn-5 | |
| Time | 20-mer | Hsn-5 | 20-mer | Hsn-5 |
| 5 min | 31 + 8 | 0 + 0 | 97 + 1 | 9 ± 2 |
| 15 min | 42 + 5 | 1 + 3 | 97 + 2 | 43 + 3 |
| 30 min | 52 + 1 | 11 + 4 | 96 + 2 | 59 + 5 |
| 45 min | 64 + 3 | 34 + 2 | 98 + 1 | 64 + 1 |
| 90 min | 74 + 6 | 42 + 3 | 100 + 0 | 71 + 7 |

Effect of Temperature on MUC7 20-mer-Induced and Hsn-5-Induced Killing

Figure 2:
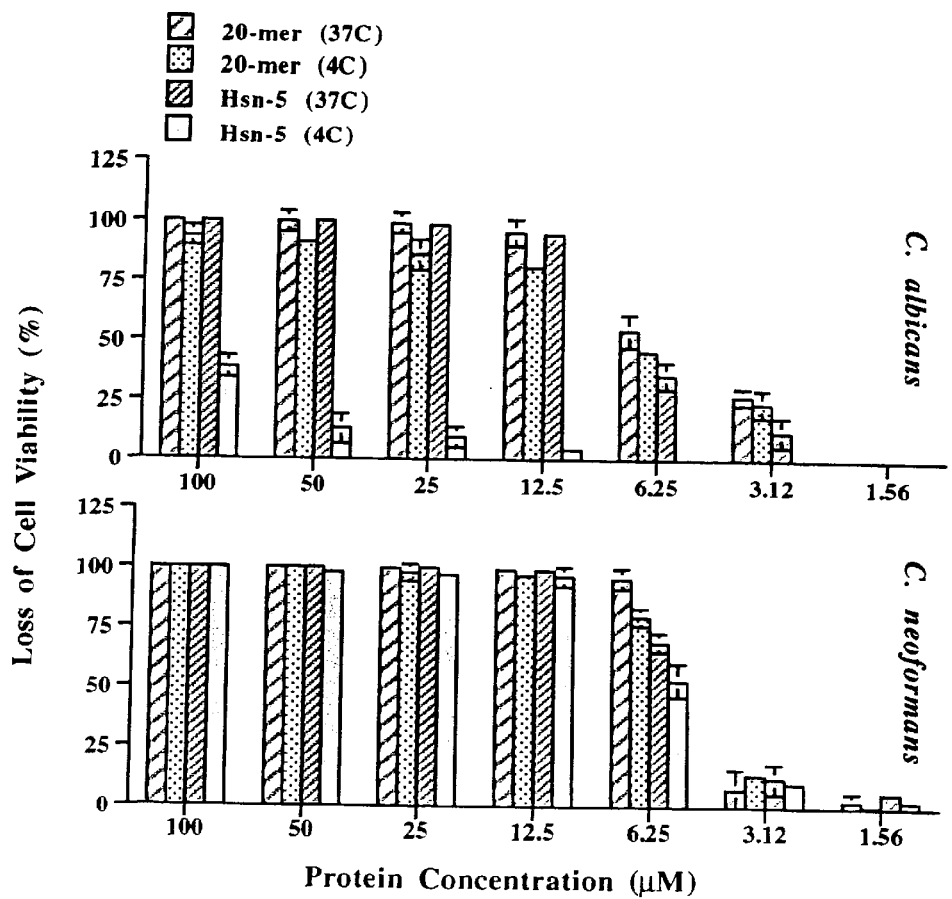
FIG. 2 is a representation of the effects of temperature on peptide-induced killing of Candida albicans and Cryptococcus neoformans for various concentrations of the 20-mer and Hsn-5 peptides at 37° C. or 4° C. Results represent the mean of duplicate or triplicate experiments.

Cidal activity assays at 4° C. were performed side by side with Hsn-5 and MUC7 20-mer, using both C. albicans and C. neoformans. The results (FIG. 2) confirmed the limited potency of Hsn-5 on C. albicans at 4° C., and revealed that MUC7 20-mer sustained almost 90% killing activity against C. albicans. The results also showed that the activities of both MUC7 20-mer and Hsn-5 against C. neoformans at 4° C. were hardly affected.

Effects of CCCP and Sodium Azide on MUC7 20-mer-Induced Killing

Figure 3:
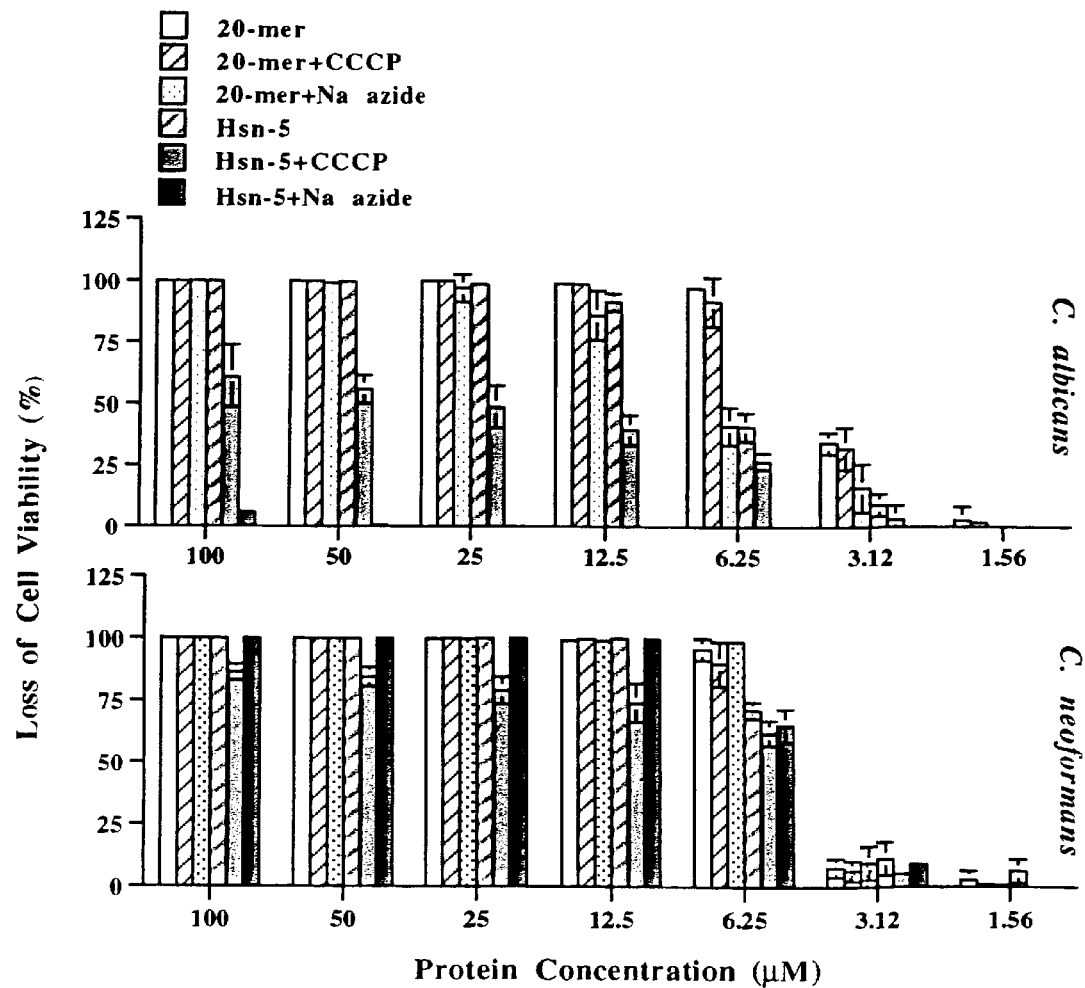
FIG. 3 is a representation of the effects of CCCP and sodium azide on peptide-induced killing of Candida albicans and Cryptococcus neoformans the 20-mer and Hsn-5 with CCCP or sodium azide. Results represent the mean of duplicate or triplicate experiments.

CCCP is an uncoupler of oxidative phosphorylation in the mitochondrial system and sodium azide inhibits ATP synthesis by inhibiting cytochrome oxidase. The results showed that the pretreatment of C. albicans or C. neoformans with CCCP or sodium azide did not protect either fungi from killing by MUC7 20-mer (FIG. 3). These results together with killing properties at 4° C. (FIG. 2) demonstrated that the fungicidal activity of MUC7 20-mer, unlike Hsn-5, does not require an active cell metabolic state. Interestingly though both CCCP and sodium azide rescued Candida cells from killing by Hsn-5, but were unable to do the same for Cryptococcus.

Effects of Divalent Cations on MUC7 20-mer-Induced Killing

Figure 4:
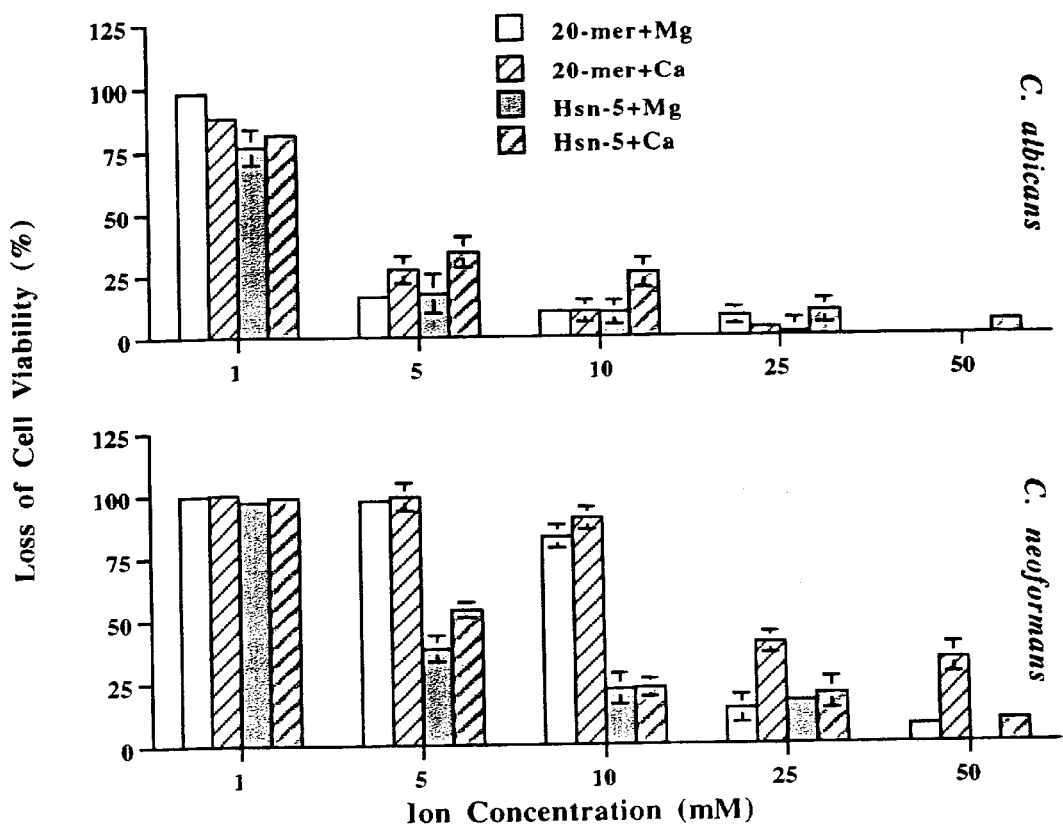
FIG. 4 is a representation of the effects of cations on peptide-induced killing of Candida albicans and Cryptococcus neoformans for the 20-mer and Hsn-5 with or without $Mg^{++}$ or $Ca^{++}$. Peptide-induced killing of both fungi in Na phosphate buffer without the cations at 25 µM concentration is 100%.

Previous studies have shown that divalent cations ($Ca^{++}$ and $Mg^{++}$) adversely affected the candidacidal activity of human neutrophilic granulocyte defensins (22) and of Hsn-5 (21). Thus the effects of $Ca^{++}$ and $Mg^{++}$ on the fungicidal activities of MUC7 20-mer were tested. Addition of either 1 mM $Ca^{++}$ (as $CaCl_2$) or $Mg^{++}$ (as $MgCl_2$) to Na phosphate buffer (10 mM, pH 7.4) had limited effect on MUC7 20-mer anticandidal activity (FIG. 4), however, an increase in concentration of these ions greatly reduced MUC7 20-mer potency. The inhibition effect of these divalent cations on antifungal activity of 20-mer was more pronounced in C. albicans. 20-mer retained 90% and 84% killing of C. neoformans in the presence of 10 mM $Ca^{++}$ or $Mg^{++}$, respectively, while it only sustained 10% anticandidal activity. Effects of MUC7 20-mer on membrane depolarization The transmembrane potentials of C. albicans and C. neoformans were monitored as 20-mer, histatin and insulin chain A (lacking antifungal activity; data not shown), were added to cell suspensions. $DiSC_3(5)$ dye release was used to monitor permeabilization (23). This cyanine dye is sensitive to membrane potential and distributes between the intracellular and extracellular space according to potential, with self-quenching occurring intracellularly. Upon permeabilization, transmembrane potential changes due to flux of ions triggering release of dye from the cell. There exists a potential dependent partition of the dye between cells and buffer. $DiSC_3(5)$ regains its fluorescent properties outside of the cell, and dye is detected by the fluorescent spectrophotometer, giving rise to the positive deflection on the readings from the samples exposed to 20-mer. Intracellular dye is not detected due to the formation of dye aggregates and quenching.

Figure 5A:
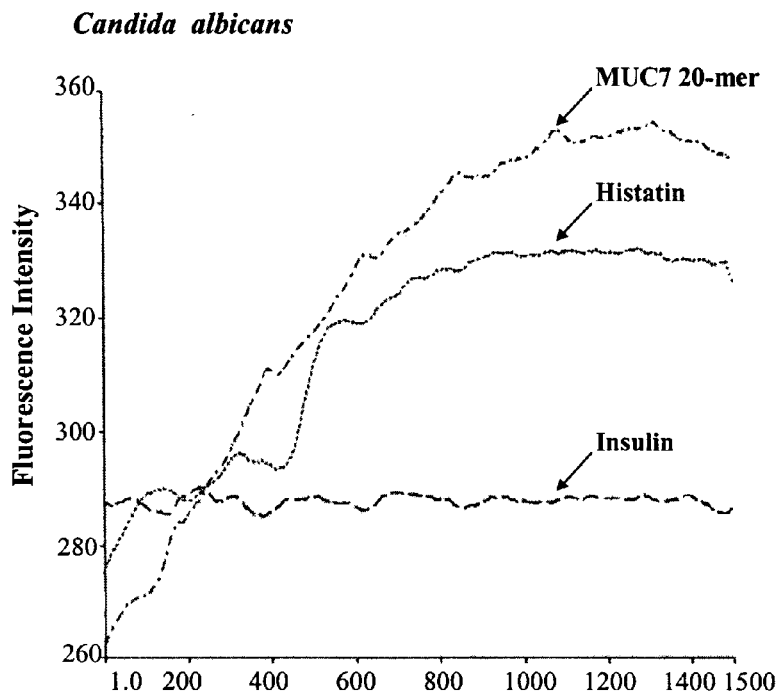
FIGS. 5A and 5B are representations of the effects of MUC7 20-mer on transmembrane potential of C. albicans (5A) and C. neoformans (5B). The fluorescence is plotted as a function of time. Peptides were added to cells at time 0, and release of dye was monitored by an increase in fluorescence.
Figure 5B:
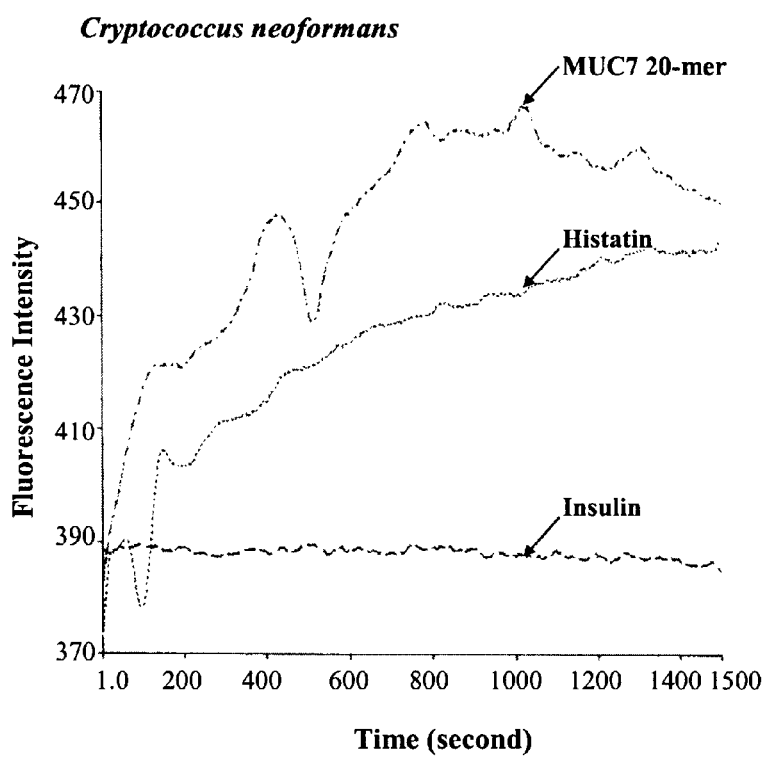

It is clear that 20-mer possesses membrane perturbing activity in C. albicans and C. neoformans as evidenced by the rapid release of dye upon addition of peptide to cells (FIG. 5). The slope of the curve generated is steep as compared to the other peptides tested, indicating a rapid and substantial release of dye, or loss of membrane potential. As expected, insulin showed little or no release of $DiSC_3(5)$ in either organism. Experiments involving histatin showed a notable release of dye but lower release than that caused by 20-mer. Differences in the effects of peptides between the two fungi are noted in that generally a greater, more rapid response is noted in C. neoformans with the peptides possessing antifungal activity.

Internalization and Localization of MUC7 20-mer

Figure 6:
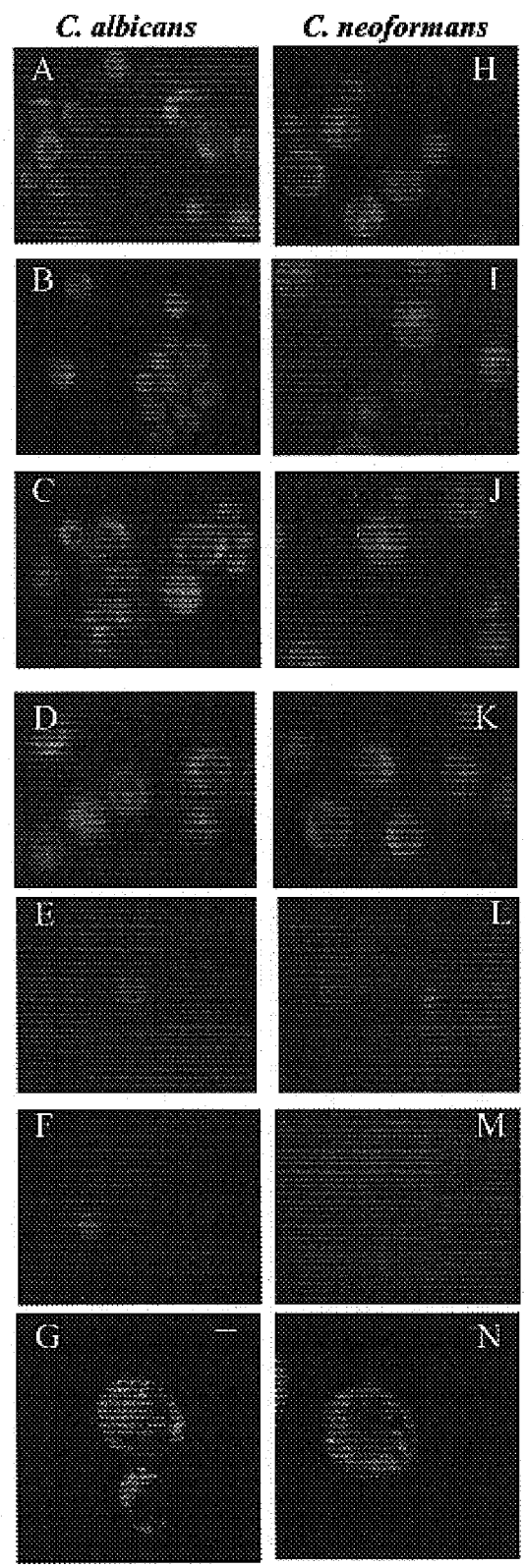
FIGS. 6A–6N are photomicrographic representations of fluorescence light microscopy of internalization of MUC7 20-mer by Candida albicans (6A–6G) and Cryptococcus neoformans (6H–6N). A and H were at 37° C.; B and I at 4° C.; C and J are cells pretreated with 20 mM sodium azide; D and K are cells pretreated with 300 µM CCCP; E and L are in the presence of 50 mM $Mg^{++}$; F and M are in the presence of 50 mM $Ca^{++}$. G and N are confocal fluorescence microscopy of Candida albicans and and Cryptococcus neoformans cells labeled with FITC-MUC7 20-mer and a mitochondria specific marker. Bar=1 µM.

In order to visualize the association of 20-mer with fungi or bacteria and its fungal cellular localization, N-terminal FITC-labeled MUC7 20-mer was used. The fungicidal activity of FITC-MUC7 20-mer is about 10% less than that of unlabeled MUC7 20mer (data not shown). FIG. 6 shows the fluorescence light micrographs of fungi for C. albicans (FIGS. 6A–6G) and C. neoformans (FIGS. 6H–6N) incubated with FITC-MUC7 20-mer, respectively. The fluorescent active peptide was visible on the cell membrane and intracellularly in both Candida and Cryptococcus, indicating that MUC7 20-mer penetrated the cell wall and cell membrane and accumulated inside of the cells. The low incubation temperature (4° C.) (FIGS. 6B and 6I) and the pretreatment of the cells with sodium azide (FIGS. 6C and 6J) and CCCP (FIGS. 6D and 6K) did not affect uptake of 20-mer. FITC labeled 20-mer was seen within all the cells with a similar fluorescence intensity as in the untreated cells. However, the uptake of the peptide is significantly limited in the presence of divalent cations, $Mg^{++}$ (FIGS. 6E and 6L) or $Ca^{++}$ (FIGS. 6F and 6M). The FITC-20-mer was only seen within a very small number of cells. The fluorescence intensity was also low. An interesting observation was that FITC-20-mer was visualized on the circumference of the cell membranes of *C. neoformans* in the presence of cations, which was not seen with *C. albicans*, indicating that the binding of the peptide to *C. neoformans* was much less affected compared to *C. albicans*. There was a greater fluorescent signal detected within the *C. neoformans* cells treated with cations than *C. albicans*. FITC labeled peptide was also seen on the cell membrane and the inside of the *A. actinomycetemcomitans* (data not shown) indicating internalization of MUC7 20-mer in bacterial cells as well. In addition, confocal fluorescence microscopy was used to study the intracellular target of the peptides. Double-labeling with FITC-labeled MUC7 20-mer and MitoTracker Red, mitochondria-specific dye, didn't show overlapping patterns, suggesting that mitochondria are not the intracellular target of MUC7 20-mer (FIGS. 6G and 6N).

The results presented here demonstrate the cidal activity of the 20-mer peptide. The observed potency of the peptide is comparable to the potency of the currently used antimicrobial agents. The 20-mer was observed to have a cidal activity at an $ED_{50}$ of about 3 $\mu$M. It is important to note that the broad-spectrum antimicrobial activity of the 20-mer peptide is specific since the control peptide, insulin chain A (also composed of 20 amino acid residues) showed no cidal activity against fungi or bacteria. Further, MUC7 20-mer showed both antifungal and antibacterial activity at micromolar concentrations with comparable activity against both in contrast to Hsn-5, which requred more than 10 fold higher concentration for killing bacteria than for killing fungi.

EXAMPLE 2

This embodiment demonstrates the antibacterial and antifungal activity of fragments of the 20-mer peptide.

Materials

Sabouraud dextrose agar (SAB) was from Difco Laboratories (Detroit, Mich.). Insulin chain A peptide was from Sigma Chemical Co. (St. Louis, Mo.). MUC7 20-mer, truncated and altered peptides were purchased from Bio-Synthesis Inc. (Lewisville, Tex.). They were (see FIG. 7): 1) unaltered 20-mer fragments: 16-mer (residue 36-51), 12-mer (residue 40-51), 11-mer (residue 41-51), 10-mer (residue 42-51), 8-mer (residue 44-51), 8-mer-N (residue 32-39, or the N-terminus); 2) altered 12-mer peptides: 12-mer-2 (Arg 40 and Lys 41 substituted by Ala), 12-mer-3 (Arg 40, Lys 41, Lys 44, Lys 48, Arg 49, and Arg 51 subsituted by Ala), and 12-mer-4 (Cys residues at position 45 and 50 were substituted by Ala). FITC-labeled 20-mer and 12-mer-3 were also purchased from Bio-Synthesis Inc. HPLC and mass spectrometry assays were performed by the company to analyze the purity of the peptides. In general, peptides' purities were between 80–99%. The purity was taken into consideration in the preparation of the stock solution of each peptide for antifungal assays. The strains of bacteria and fungi and culture conditions were as described in Example 1.

Antifungal Activity Assays

Two fold serial dilutions of each peptide (ranging from 50 or 25 $\mu$M down to 1.5625 $\mu$M) in 20 $\mu$l of 10 mM Na phosphate buffer, pH 7.4, were incubated with an equal volume of fungal strain ($10^5$ cells/ml, also in Na phosphate buffer) for 1.5 hours at 37°. At the end of incubation, the samples were diluted 20 fold with the same buffer and aliquots (~150 cells) of each sample were plated on SAB plates. Plates were incubated for 1 to 2 days for *C. albicans* and *C. neoformans*, respectively. Colonies were then counted, and the loss of cell viability was plotted as a function of protein concentration. The statistical analysis was as described in Example 1.

Fluorescence Light Microscopy

The internalization of MUC7 20-mer and 12-mer-3 into fungi was visualized using FITC labeled peptides. Cells ($10^7$) were treated with 50 $\mu$M FITC-MUC7 20-mer or 12-mer-3 for 45–90 mins in 100 $\mu$l of Na phosphate buffer (10 mM, pH 7.4) at 37° C. The cells were then processed and visualized as described in Example 1.

Results

In order to determine if shorter peptides of the 20-mer could also be used for the present invention, and to determine their location, truncation at the N-terminus of the 20-mer (with the net positive charge of 7) since the N-terminus lacks the positively charged residues were made. The analysis was done with five N-truncated peptides (see FIG. 7): 16-mer, 12-mer, 11-mer, 10-mer, and 8-mer, with the net positive charge of 7, 6, 5, 4 and 4, respectively.

Figure 8:
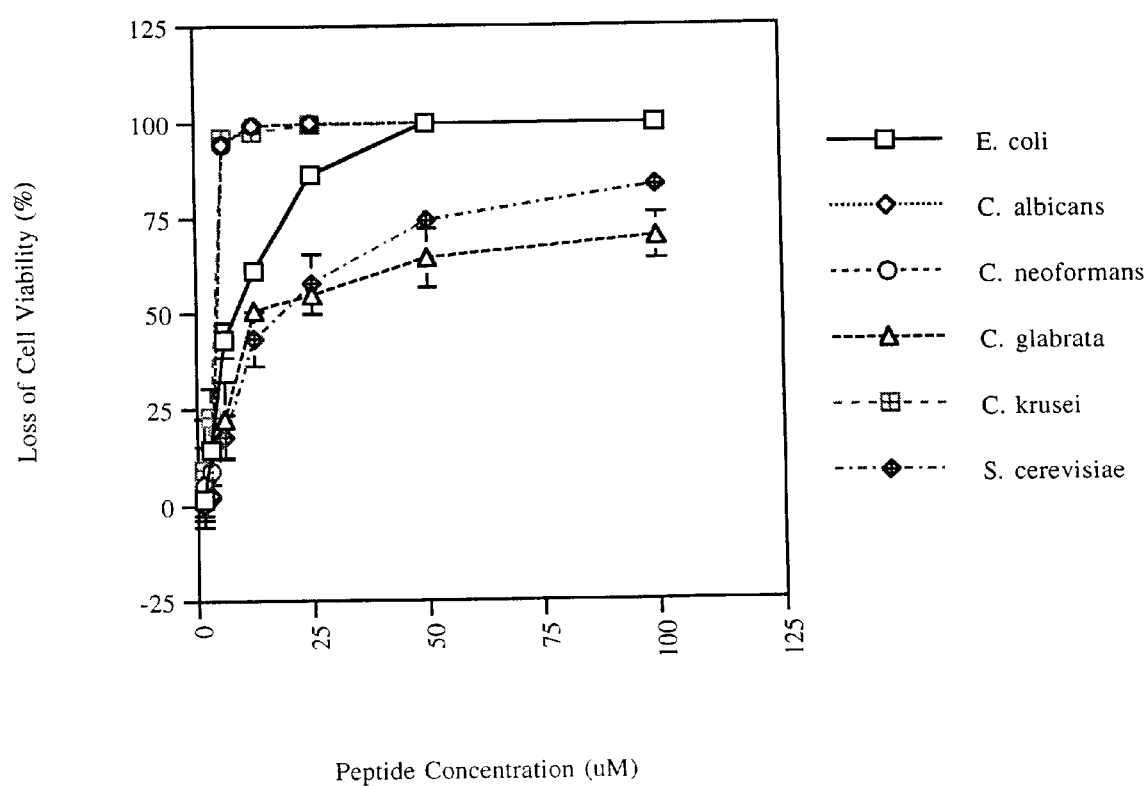
FIG. 8 is a representation of the antifungal and antibacterial activity of MUC 12-mer of SEQ ID NO:6 plotted as peptide concentration versus loss of cell viability.
Figure 9:
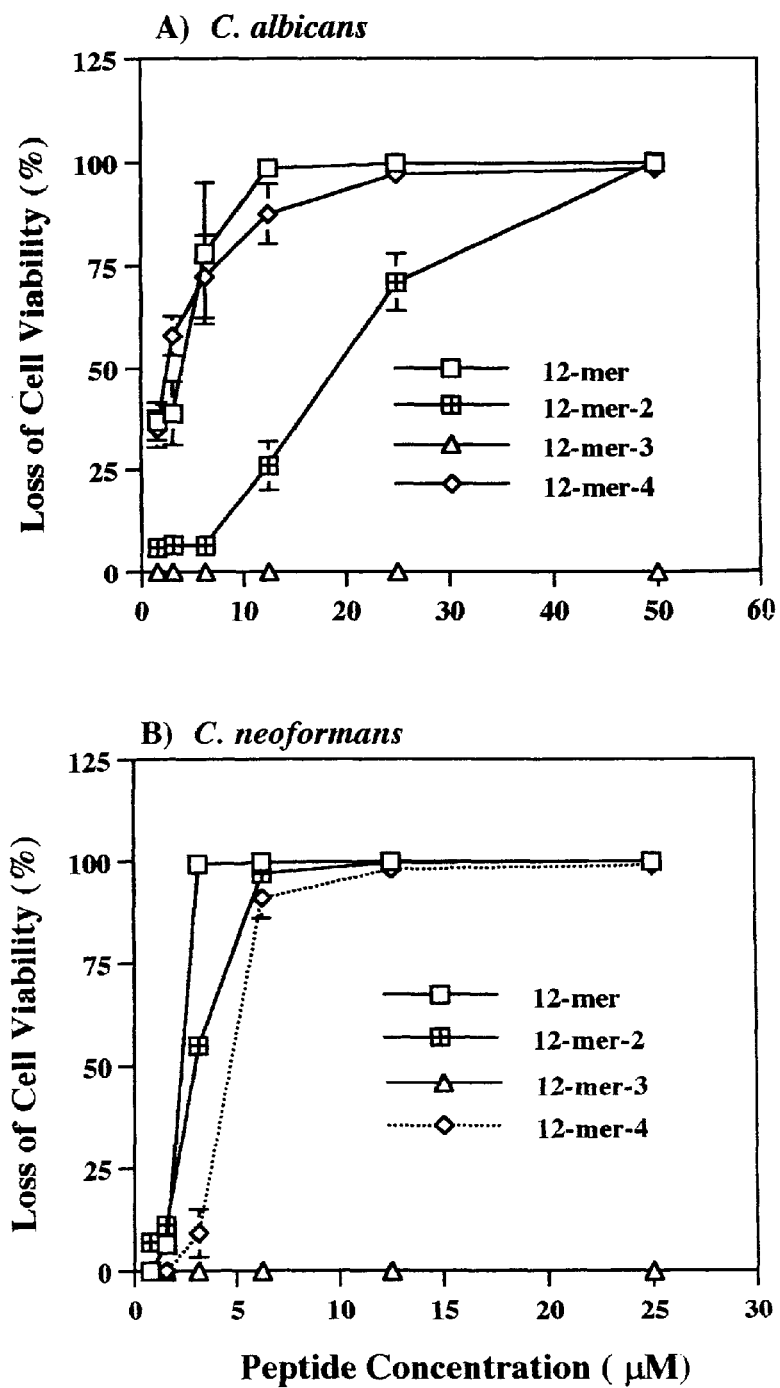
FIGS. 9A and 9B are representations of fungicidal activity of the fragments of the MUC7 20-mer peptide plotted as peptide concentration versus loss of cell viability for C.

The 12-mer peptide was active against a variety of fungi and bacteria as shown in FIG. 8. The dose response curves are shown in FIGS. 9A (*C. albicans*) and 9B (*C. neoformans*) and the $ED_{50}$ values are shown in Table 3.

TABLE 3

Amino acid sequences and $ED_{50}$ of unaltered MUC7 20-mer and truncated peptides

| Peptide | Seq. ID No. | Net positive charge | $ED_{50}$ $\mu$M (95% confidence limit) | |
|---|---|---|---|---|
| | | | *C. albicans* | *C. neoformans* |
| 20-mer: | Seq. ID No. 4 | 7 | 5.8 (4.2–8.7) | 6.7 (6.1–7.4)[a] |
| 16-mer: | Seq. ID No. 5 | 7 | 6.9 (4.8–9.5) | 5.3 (4.1–6.7) |
| 12-mer: | Seq. ID No. 6 | 6 | 2.1 (1.3–3.2) | 2.1 (1.8–2.5) |
| 11-mer: | Seq. ID No. 7 | 5 | 3.26 (1.9–5.6) | 4.5 (2.6–14.2) |
| 10-mer: | Seq. ID No. 8 | 4 | 20.7 (17.7–24.6) | 5.6 (2.3–19.4) |
| 8-mer: | Seq. ID No. 9 | 4 | 23.2 (13.4–58.6) | 5.8 (2.7–15.8) |
| 8-mer-N: | Seq. ID No. 10 | 1 | No activity | No activity |

[a]The data on MUC7 20-mer is from our previously published study (7)

The data presented here indicates that 16-mer (with the net positive charge of 7, same as 20-mer) has a comparable activity to that of 20-mer against both *C. albicans* ($ED_{50}$ of 6.9 $\mu$M for 16-mer, versus 5.8 $\mu$M for 20-mer) and *C. neoformans* ($ED_{50}$ 5.3 $\mu$M for 16-mer, versus 6.7 $\mu$M for 20-mer). Interestingly though, 12-mer (with the net positive charge of 6) possesses increased activity against both fungi (showing $ED_{50}$ of 2.1 $\mu$M for both). The 11-mer (with the net positive charge of 5) exhibits comparable activity to that of 12-mer against *C. albicans* (the $ED_{50}$ values of the 12-mer and 11-mer overlap), but slightly lower against *C. neoformans* (the $ED_{50}$ values do not overlap). The activities of 10-mer and 8-mer (the net positive charge of 4 in both) against *C. albicans* decreased ($ED_{50}$ of 20.7 $\mu$M and 23.2 $\mu$M, respectively) but against *C. neoformans* remained comparable to that of 11-mer (the $ED_{50}$ values for all 3 peptides overlap). Because even the 8-mer possessed considerable activity against *C. neoformans*, a peptide of the same length from another region was tested for antifungal activity. Thus, N-terminal 8-mer (with the net positive charge of 1) was custom-synthesized and tested. As shown in FIGS. 9A and B and Table 3, this 8-mer showed no antifungal activity. Additionally, an unrelated peptide, Insulin chain A (21 aa residues) showed also no activity (data not shown).

Further the effect of net positive charge of 12-mer on its cidal activity against *C. albicans* and *C. neoformans* was examined by preparing variants. The variants are listed in Table 4. The fungicidal activities are shown in FIGS. 10A and B and $ED_{50}$ values in Table 4. MUC712-mer has a net positive charge of 6 (versus 7 in the 20-mer). Its $ED_{50}$ value against both fungi is 2.1 µM. When the first and second positive aa residues (Arg and Lys) of 12-mer were substituted with Ala (12-mer-3), the $ED_{50}$ value of this variant against C. albicans dropped to 14.6 µM. When all 6 positively charged residues were replaced by Ala (12-mer-3), there was no anticandidal activity observed. On the other hand, the $ED_{50}$ value of 12-mer-2 against C. neoformans remains comparable to that of unaltered 12-mer; cidal activity was diminished only when 6 positively charged residues were all replaced by Ala (12-mer-3). These data indicate that at least one net positive charge is required for activity.

TABLE 4

Amino acid sequences and $ED_{50}$ of unaltered MUC7 12-mer and truncated peptides

| Peptides | Seq. ID No. | Net positive charge | $ED_{50}$ µM (95% confidence limit) C. albicans | C. neoformans |
|---|---|---|---|---|
| 12-mer: | Seq. ID No. 6 | 6 | 2.1 (1.3–3.2) | 2.1 (1.8–2.5) |
| 12-mer-2: | Seq. ID No. 11 | 4 | 14.6 (8.7–31.8) | 2.2 (1.8–2.6) |
| 12-mer-3: | Seq. ID No. 12 | 0 | No activity | No activity |
| 12-mer-4: | Seq. ID No. 13 | 6 | 2.0 (0.8–3.7) | 2.5 (1.6–3.9) |

It was previously reported that rNMUC7 (recombinant protein consisting of the N-terminal 144 residues of MUC7) bound to Streptococcus mutans (S. mutans) and alkylation of the two Cys residues (Cys45 and Cys50) resulted in the complete loss of bacterial binding (8). This suggests that binding of MUC7 to S. mutans occurs between the N-terminal region of the mucin molecule and the surface of bacteria, and that the binding is dependent on a cysteine-containing domain within this region of MUC7. To examine if the two Cys residues also play a role in fungicidal activity of MUC7 12-mer, 12-mer-4 with the two Cys residues substituted with Ala was designed and custom-synthesized. Interestingly, this substitution did not alter 12-mer antifungal activity, indicating that the Cys residues are not important for cidal activity against both C. albicans and C. neoformans.

Since the 12-mer-3 was not found to be effective, it is believed that for the peptides of the present invention to be useful a net positive charge is required. The fluorescence light microscopy study confirmed this hypothesis. As shown in FIGS. 11A–F, after incubating the fungal cells (C. albicans and C. neoformans) with FITC-12-mer-3, the fluorescent active 12-mer-3 was not visible either on the cell membrane or inside of both Candida and Cryptococcus cells, while FITC-20-mer (serving as a positive control) was, indicating that MUC7 12-mer-3, with 0 net positive charge, is not able to interact with the cell membrane and subsequently be taken-up by these cells.

The data presented herein indicate that peptides obtained from the C-terminus of the MUCD1 domain or variants thereof can be used as antifungal and antibacterial agents. This property is specific for the C-terminus of the MUC7D1 peptide since the 15-mer (amino acids 3–17) and the 8-mer-N (amino acids 32–39) did not exhibit antibacterial activity.

References 1. van't Hof, W., E. C. Veerman, E. J. Helmerhorst, and A. V. Amerongen. 2001. Antimicrobial peptides: properties and applicability. Biol. Chem. 382: 597–619.
2. Lehrer, R. I., and T. Ganz. 1999. Antimicrobial peptides in mammalian and insect host defence. Curr. Opin. Immunol. 11: 23–27.
3. Zasloff, M. 1987. Magainins, a class of antimicrobial peptides from Xenopus skin: isolation, characterization of two active forms, and partial cDNA sequence of a precursor. Proc. Natl. Acad. Sci. U.S.A. 84: 5449–5453.
4. Mor, A., V. H. Nguyen A. Delfour, D. Migliore-Samour, and P. Nicolas. 1991. Isolation, amino acid sequence, and synthesis of dermaseptin, a novel antimicrobial peptide of amphibian skin. Biochemistry 30, 8824–8830.
5. Steiner, H., D. Hultmark, A. Engstrom, H. Bennich, and H. G. Boman. 1981. Sequence and specificity of two antibacterial proteins involved in insect immunity. Nature 292: 246–248.
6. De Lucca, A. J. 2000. Antifungal peptides: potential candidates for the treatment of fungal infections. Expert Opin. Investig. Drugs. 9: 273–299.
7. Shai, Y. 1999. Mechanism of the binding, insertion and destabilization of phospholipid bilayer membranes by alpha-helical antimicrobial and cell non-selective membrane-lytic peptides. Biochim. Biophys. Acta 1462: 55–70.
8. Tabak, L. A. 1995. In defense of the oral cavity: structure, biosynthesis, and function of salivary mucins. Annu. Rev. Physiol. 57: 547–564.
9. Tabak, L. A. 1998. Protein structure and function relationships: mucins, p. 189–197. In Guggenheim, B., and S. Shapiro (ed.), Oral Biology at the Turn of the Century (Misconceptions, Truths, Challenges and Prospects), Karger A G, Basel (Switzerland).
10. Gibbons, R. J., and J. V. Qureshi. 1978. Selective binding of blood group-reactive salivary mucins by Streptococcus mutans and other oral organisms. Infect. Immun. 22: 665–671.
11. Mandel, I. D. 1987. The functions of saliva. J. Dent. Res. 66: 623–627.
12. Oppenheim, F. G., T. Xu, F. M. McMillian, S. M. Levitz, R. D. Diamond, G. D. Offner, and R. F. Troxler. 1988. Histatins, a novel family of histidine-rich proteins in human parotid secretion. Isolation, characterization, primary structure, and fungistatic effects on Candida albicans. J. Biol. Chem. 263: 7472–7477.
13. Koshlukova, S. E., M. W. Araujo, D. Baev, and M. Edgerton. 2000. Released ATP is an extracellular cytotoxic mediator in salivary histatin 5-induced killing of Candida albicans. Infect. Immun. 68: 6848–6856.
14. Koshlukova, S. E., T. L. Lloyd, M. W. Araujo, and M. Edgerton. 1999. Salivary histatin 5 induces non-lytic release of ATP from Candida albicans leading to cell death. J. Biol. Chem. 274:18872–18879.
15. Edgerton, M., S. E. Koshlukova, M. W. Araujo, R. C. Patel, J. Dong, and J. A. Bruenn. 2000. Salivary histatin 5 and human neutrophil defensin 1 kill Candida albicans via shared pathways. Antimicrob. Agents Chemother. 44: 3310–3316.
16. Merrifield, J. J. Biol. Chem., J. Am. Chem. Soc. 85:2149, 1963.
17. Sambrook et a., Molecular Cloning: A Laboratory Manual, 2nd ed., Cold Spring Harbor Laboratory Press, Cold Spring Harbor, N.Y., 1989.
18. Ausubel et al. (eds.), Current Protocols in Molecular Biology, John Wiley and Sons, Inc., NY, 1987.
19. Tsai, H., and L. A. Bobek. 1997. Studies of the mechanism of human salivary histatin-5 candidacidal activity with histatin-5 variants and azole-sensitive and —resistant Candida species. Antimicrob. Agents Chemother. 41: 2224–2228.
20. Situ, H., and L. A. Bobek. 2000. In vitro assessment of antifungal therapeutic potential of salivary histatin-5, two variants of histatin-5, and salivary mucin (MUC7) domain 1. *Antimicrob Agents Chemother* 44: 1485–1493.
21. Patel, R., S. E. Koshlukova, T. L. Lloyd, M. W. Araujo, and M. Edgerton. 1999. Candidacidal activity of salivary Hsts in physiologic inorganic ion buffer. *J. Dent. Res.* 78: 342.
22. Lehrer, R. I., T. Ganz, D. Szklarek, and M. E. Selsted. 1988. Modulation of the in vitro candidacidal activity of human neutrophil defensins by target cell metabolism and divalent cations. *J. Clin. Investig.* 81: 1829–1835.
23. Wu, M., E. Maier, R. Benz, and R. E. W. Hancock. 1999. Mechanism of interaction of different classes of cationic antimicrobial peptides with planar bilayers and with the cytoplasmic membrane of *Escherichia coli*. *Biochemistry* 38: 7235–7242.

I claim:

1. An isolated and purified peptide consisting of SEQ ID NO:4 or fragments thereof selected from the group consisting of SEQ ID NO:5, SEQ ID NO:6, SEQ ID NO:7, SEQ ID NO:8 and SEQ ID NO:9.

2. The peptide of claim 1, wherein the peptide consists of SEQ ID NO:5.

3. The peptide of claim 1, wherein the peptide consists of SEQ ID NO:6.

4. The peptide of claim 1, wherein the peptide consists of SEQ ID NO:7.

5. The peptide of claim 1, wherein the peptide consists of SEQ ID NO:8.

6. The peptide of claim 1, wherein the peptide consists of SEQ ID NO:9.

7. An isolated and purified peptide consisting of SEQ ID NO:13.

8. An isolated and purified peptide consisting of SEQ ID NO:11.

* * * * *

UNITED STATES PATENT AND TRADEMARK OFFICE
CERTIFICATE OF CORRECTION

PATENT NO. : 6,790,833 B2  
DATED : September 14, 2004  
INVENTOR(S) : Libuse Bobek It is certified that error appears in the above-identified patent and that said Letters Patent is hereby corrected as shown below:

Column 1,  
Line 6, insert:  
-- This work was supported by Government funding under Grant No. R01 DE09820 from the National Institutes of Health. The Government has certain rights in the invention. --.

Signed and Sealed this

Thirty-first Day of January, 2006

JON W. DUDAS  
*Director of the United States Patent and Trademark Office*